United States Patent
Samain et al.

(10) Patent No.: US 6,221,347 B1
(45) Date of Patent: *Apr. 24, 2001

(54) COSMETIC COMPOSITION BASED ON NONIONIC GUAR GUM AND ON NON-CROSSLINKED ANIONIC POLYMER

(75) Inventors: Henri Samain, Bièvres; Isabelle Cretois, Clichy, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,580

(22) PCT Filed: Jan. 23, 1996

(86) PCT No.: PCT/FR96/00110

§ 371 Date: Oct. 2, 1996

§ 102(e) Date: Oct. 2, 1996

(87) PCT Pub. No.: WO96/23482

PCT Pub. Date: Aug. 8, 1996

(30) Foreign Application Priority Data

Feb. 2, 1995 (FR) .................................................. 95 01228

(51) Int. Cl.[7] .............................. A61K 7/06; A61K 7/11; A61K 7/00
(52) U.S. Cl. ................. 424/70.31; 424/70.1; 424/78.03; 424/401; 524/55
(58) Field of Search ............................... 424/401, 78.03, 424/70.31, 70.1; 524/55

(56) References Cited

U.S. PATENT DOCUMENTS

| 4,491,539 | 1/1985 | Hoskins et al. . | |
|---|---|---|---|
| 4,540,510 | 9/1985 | Karl . | |
| 4,591,610 | 5/1986 | Grollier . | |
| 4,744,977 | * 5/1988 | Hensen | 424/70 |
| 4,929,690 | * 5/1990 | Goertz | 525/366 |
| 5,100,658 | 3/1992 | Bolich, Jr. et al. . | |
| 5,243,021 | * 9/1993 | Langer | 528/272 |
| 5,389,279 | * 2/1995 | Au | 252/108 |
| 5,618,529 | * 4/1997 | Pichierri | 424/401 |
| 5,698,183 | * 12/1997 | Langer | 424/59 |

FOREIGN PATENT DOCUMENTS

| 0 152 095 | 8/1985 | (EP) . |
| 0 412 705 | 2/1991 | (EP) . |
| 2 542 997 | 9/1984 | (FR) . |
| 0 320 218 | 6/1989 | (FR) . |
| 2 670 673 | 6/1992 | (FR) . |
| 2 136 689 | 9/1984 | (GB) . |
| 5-345708 | 12/1993 | (JP) . |
| WO 92/21316 | 12/1992 | (WO) . |

OTHER PUBLICATIONS

Hawley's Condensed Chemical Dictionary—Feb. 12, 1991 pp. 95, 224, 225, 237, 580, 581, 669, 670, 1169.*
Patent Abstracts of Japan (JP 5345708), vol. 18, No. 191, Apr. 4, 1994.

* cited by examiner

*Primary Examiner*—Fred Zitomer
(74) *Attorney, Agent, or Firm*—Finnegan, Henderson, Farabow, Garrett & Dunner, L.L.P.

(57) ABSTRACT

The present invention relates to non-washing cosmetic compositions containing, in a cosmetically acceptable medium, at least one nonionic guar gum and at least one non-crosslinked anionic polymer.

The invention also relates to a process for the cosmetic treatment of keratin substances, such as the hair or the eyelashes, characterized in that it consists in applying a cosmetic composition as defined above to the keratin substances, and then possibly in rinsing with water.

17 Claims, No Drawings

COSMETIC COMPOSITION BASED ON NONIONIC GUAR GUM AND ON NON-CROSSLINKED ANIONIC POLYMER

The present invention relates to non-washing cosmetic compositions containing, in a cosmetically acceptable medium, at least one nonionic guar gum and at least one non-crosslinked anionic polymer.

The invention also relates to a process for the non-washing cosmetic treatment of keratin substances, such as the hair or the eyelashes, characterized in that it consists in applying a cosmetic composition as defined above to the keratin substances, and then possibly in rinsing with water.

Formulations which allow the hair to be fixed and conditioned are already known in the state of the art. With this aim, compositions in gel form which are generally based on crosslinked acrylic polymers have already been used. However, these compositions have the drawback of leaving an undesirable deposit on the hair, which damages its cosmetic properties: thus, at the end of the operation, the hair lacks sheen, is coarse or is sticky.

Anionic polymers known to afford shape retention and/or fixing to the head of hair have also been combined with cationic polymers, in particular cationic guar gums. However, the Applicant has observed in particular that the hair had an unpleasant feel and that the hairstyle shape retention was low.

Furthermore, the products based on anionic polymers often have problems associated with the texture of the product. Indeed, it is difficult to obtain products that spread well on the hair.

Nonionic guar gums are described as being thickeners.

The Applicant has just discovered, in fact, that the combination of nonionic guar gums with non-crosslinked anionic polymers leads, unexpectedly and surprisingly, to particularly advantageous properties, in particular to an improvement in the hairstyle shape retention over time and in the fixing power. The head of hair has more volume and the hair is shiny and has a natural feel.

Furthermore, these compositions spread more easily on the hair and the composition has a more pleasant texture.

This discovery forms the basis of the present invention.

The subject of the present invention is thus novel, non-washing cosmetic compositions for keratin substances such as the hair, the skin or the eyelashes, containing, in a non-detergent cosmetically acceptable medium, at least one nonionic guar gum and at least one non-crosslinked anionic polymer chosen from:

(A)—Copolymers comprising (i) one or more maleic, fumaric or itaconic acids or anhydrides and (ii) at least one monomer chosen from vinyl esters, vinyl ethers, vinyl halides, phenylvinyl derivatives, and acrylic acid and esters thereof;

Copolymers comprising (i) one or more maleic, citraconic or itaconic anhydrides and (ii) one or more monomers chosen from allylic or methallylic esters optionally containing one or more acrylamide, methacrylamide or α-olefin group, acrylic or methacrylic esters, acrylic acid or methacrylic acid or vinylpyrrolidone in their chain, the anhydride functions of these copolymers optionally being monoesterified or monoamidated.

(B)—Copolymers of acrylic acid or of methacrylic acid with one or more monoethylenic monomers such as ethylene, styrene, vinyl esters, acrylic acid esters or methacrylic acid esters.

(C)—Copolymers comprising (i) one or more acrylic or methacrylic acids, (ii) one or more monoethylenic monomers such as ethylene, styrene, vinyl esters, acrylic acid esters or methacrylic acid esters and (iii) one or more monomers chosen from vinyllactams, optionally polyoxyalkylenated C6–C22 alkyl allyl or methallyl ethers, vinyl acetate and N-alkyl(C3–C10) acrylamides.

Other characteristics, aspects, subjects and advantages of the invention will emerge even more clearly on reading the description and the examples which follow.

According to the invention, the expression non-washing compositions is understood to denote compositions having no detergent nature. The compositions preferably contain less than 4% by weight of detergent surfactants.

According to the invention, chemically modified or unmodified nonionic guar gums may be used.

The unmodified nonionic guar gums are, for example, the products sold under the name Vidogum GH 175 by the company Unipectine and under the name Jaguar C by the company Meyhall.

The nonionic guar gums which can be used according to the invention are preferably modified by $C_1$–$C_6$ hydroxyalkyl groups.

Among the hydroxyalkyl groups which may be mentioned as examples are hydroxymethyl, hydroxyethyl, hydroxypropyl and hydroxybutyl groups.

These guar gums are well known in the state of the art and may be prepared, for example, by reacting corresponding alkene oxides, such as propylene oxides for example, with guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2 plus.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhône-Poulenc (Meyhall) or under the name Galactasol 4H4FD2 by the company Aqualon.

According to the invention, anionic polymers containing groups derived from carboxylic acid preferably having a molecular weight of approximately between 500 and 5,000,000 may be used.

The polymers of group (A) are described in particular in U.S. Pat. Nos. 2,047,398, 2,723,248 and 2,102,113 and GB patent 839,805 and are, in particular, the products sold under the names Gantrez AN or ES by the company ISP. Polymers of group (A) are also, for example, described in French patents 2,350,384 and 2,357,241 by the Applicant. The teaching of these patents is included in the present application.

The polymers of group (B) are described in particular in French patent 1,222,944 and German application 2,330,956.

The acrylic or methacrylic acid esters are, for example, the $C_1$–$C_{20}$ alkyl acrylates or methacrylates.

Among the polymers of group (B), copolymers of methacrylic acid and of $C_1$–$C_6$ alkyl acrylate and copolymers of acrylic or methacrylic acid, of alkyl acrylate or methacrylate and of styrene are preferred.

In the copolymers of group (C), the acrylic or methacrylic acid esters are, for example, $C_1$–$C_{20}$ alkyl acrylates or methacrylates.

Among the monomers (iii), the vinyllactams are, for example, vinylpyrrolidone or vinylcaprolactam. The allyl or methallyl ethers are, for example, polyoxyalkylenated C12–C22 alkyl allyl ethers.

The number of alkylene oxide groups may range from 2 to 100. The alkylene oxides preferably have 2 or 3 carbon atoms.

Among the monomers (iii) which are preferred more particularly are polyoxyethylenated stearyl allyl ether and vinylpyrrolidone.

The copolymers of group (C) are, for example, copolymers of acrylic or methacrylic acid, of alkyl acrylate or methacrylate and of N-tert-butylacrylamide, terpolymers of vinylpyrrolidone/acrylic acid/lauryl methacrylate, and terpolymers of methacrylic acid, of ethyl acrylate and of stearyl allyl ether polyoxyethylenated with 10 mol of ethylene oxide.

According to the invention, the anionic polymers of group (A) are preferably chosen from copolymers comprising (i) maleic, fumaric or itaconic acids or anhydrides, (ii) vinyl esters, vinyl ethers, vinyl halides, phenylvinyl derivatives, and acrylic acid and esters thereof, such as the copolymers methyl vinyl ether/maleic anhydride monoesterified with $C_1$–$C_6$ alcohols, sold under the names Gantrez by the company ISP.

Copolymers of methyl vinyl ether/maleic anhydride monoesterified with butanol, sold under the name Gantrez ES 425 by the company ISP, copolymers of methacrylic acid and of $C_1$–$C_6$ alkyl acrylate such as ethyl acrylate, sold for example under the name Luvimer MAE or MAEX by the company BASF, and terpolymers of vinylpyrrolidone/acrylic acid/lauryl methacrylate, sold for example under the name Acrylidone LM by the company ISP, are preferably used.

The concentration of nonionic guar gum may range between 0.01% and 5% by weight approximately relative to the total weight of the composition, and preferably between 0.1 and 2.5% approximately.

The concentration of non-crosslinked anionic polymer may range between 0.01 and 8% by weight approximately relative to the total weight of the composition, and preferably between 0.1 and 3% approximately.

The nonionic guar gum/non-crosslinked anionic polymer weight ratio is preferably less than 1.

The cosmetically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and isopropanol, polyalcohols such as diethylene glycol, glycol ethers, glycol alkyl ethers or diethylene glycol alkyl ethers.

The pH of the compositions according to the invention is generally between 2 and 9 and in particular between 3 and 8. It may be adjusted to the chosen value by means of basifying or acidifying agents usually used in cosmetics for this type of application.

The compositions according to the invention may also contain thickeners, surfactants, preserving agents, sequestering agents, softeners, fragrances, dyes, viscosity modifiers, foam modifiers, foaming agents, foam stabilizers, pearlescent agents, moisturizing agents, antidandruff agents, antiseborrhoeic agents, sunscreens, proteins, vitamins, plasticizers, hydroxy acids, electrolytes, propellants and fragrances.

The compositions according to the invention may also contain conditioners. In this case, these conditioners may be chosen from natural or synthetic oils and waxes, fatty alcohols, polyhydric alcohol esters, glycerides, silicone oils, gums and resins or mixtures of these various compounds.

The subject of the invention is also a process for the treatment of the skin or keratin fibres, such as the hair or the eyelashes, characterized in that it consists in applying a cosmetic composition as defined above to the skin or to the keratin fibres, and then possibly in rinsing with water, after an optional period of leaving the applied composition in place.

Thus, this process according to the invention makes it possible to retain the shape of the hairstyle or of the eyelashes and to treat and care for the skin, the hair or any other keratin substance.

The cosmetic compositions according to the invention may be in the form of a gel, a milk, a cream, a cream-gel a spray, a relatively thickened lotion or a mousse and may be used, for example, for the skin, the hair, the eyelashes or the eyebrows.

For the hair, they are more particularly rinse-out or leave-in compositions, to be applied before or after shampooing, dyeing, bleaching, permanent-waving or straightening the hair.

The compositions may also be hair setting. lotions, blow-drying lotions and fixing and styling compositions.

The lotions may be packaged in various forms, in particular in vaporizers, pump-dispenser bottles or in aerosol containers so as to ensure application of the composition in vaporized form or in the form of a mousse. Such packaging forms are indicated, for example, when it is desired to obtain a spray, a lacquer or a mousse for fixing or treating the hair.

When the composition according to the invention is packaged in aerosol form for the purpose of obtaining an aerosol mousse or lacquer, it comprises at least one propellant which may be chosen from volatile hydrocarbons such as n-butane, propane, isobutane, chloro and/or fluoro hydrocarbons and mixtures thereof. Carbon dioxide, nitrous oxide, dimethyl ether, nitrogen or compressed air may also be used as propellant.

In all of the preceding text and in the following text, the percentages expressed are by weight.

The invention will now be illustrated more fully with the aid of the examples which follow, which should not be considered as limiting it to the embodiments described.

In the examples, AM means active material.

EXAMPLE 1

A gel (1), in accordance with the invention, of the following composition was prepared:

| | |
|---|---|
| Nonionic guar gum modified with hydroxypropyl groups, sold under the trade name Jaguar HP60 by the company Meyhall | 0.95 g |
| Methyl vinyl ether/butyl monomaleate copolymer 100% neutralized with AMP (Gantrez ES 425 from ISP) | 2 g AM |
| Water | qs 100 g |

A comparative gel (2) of the following composition was prepared:

| | |
|---|---|
| Cationic guar gum sold under the trade name Jaguar C13S by the company Meyhall | 0.95 g |
| Gantrez ES 425 100% neutralized with AMP (ISP) | 2 g AM |
| Water | qs 100 g |

A comparative gel (3) of the following composition was prepared:

| | |
|---|---|
| Crosslinked acrylic acid polymer gold under the trade name Carbopol 940 by the company Goodrich | 0.95 g |
| Gantrez ES 425 (ISP) | 2 g |
| Monoethanolamine | qs pH 7 |
| Demineralized water | qs 100 g |

A comparative gel (4) of the following composition was prepared:

| | |
|---|---|
| Vinyl acetate/vinylpyrrolidone copolymer sold under the trade name Luviskol VA 64 by the company BASF | 0.95 g |
| Gantrez ES 425 (ISP) 100% neutralized with AMP | 2 g AM |
| Water | qs 100 g |

0.5 g of gel per g of hair was applied to locks of washed and towel-dried hair. The hair was then blow-dried.

A panel of 8 judges was then asked to evaluate the holding of the style (hardening of the fibre) and the feel of the hair.
Rating:

Holding of the style: 0 (no holding) to 5 (very strong fixing)

Feel: 0 (very poor) to 5 (excellent)

After 5 hours at ambient temperature and humidity, the same judges evaluated the hairstyle shape retention.
Rating:

Hold: 0 (no hold) to 5 (perfect hold)

The results (average of the ratings) are collated in the following table:

| | Holding of the style | Feel | Shape retention |
|---|---|---|---|
| Gel (1) Invention | 4 | 4 | 4 |
| Gel (2) Comparative | 2.25 | 0.75 | 1.25 |
| Gel (3) Comparative | 2 | 0.75 | 1.5 |
| Gel (4) Comparative | 4 | 0.5 | 2.75 |

Only gel 1 according to the invention has very good style-holding, feel and shape-retention properties.

EXAMPLE 2

A gel according to the invention having the following composition was prepared:

| | |
|---|---|
| Nonionic guar gum modified with hydroxypropyl groups, sold under the trade name Jaguar HP60 by the company Meyhall | 1.45 g |
| Anionic polymer 100% neutralized with AMP | 1.5 g AM |
| Water | qs 100 g |

Anionic Polymer:

Gel (5) : Gantrez ES 425 (ISP)

Gel (6) : Acrylic acid/ethyl acrylate copolymer (Luvimer from BASF)

0.5 g of gel per g of hair was applied to locks of washed and towel-dried hair. The hair was then blow-dried.

A panel of 8 judges was then asked to evaluate the holding of the style, the feel and the hairstyle shape retention.

The results (average of the ratings) are collated in the following table:

| | Holding of the style | Feel | Shape retention |
|---|---|---|---|
| Gel (5) | 4 | 3.75 | 3.75 |
| Gel (6) | 4 | 4 | 4 |

The gels according to the invention have good style-holding, feel and shape-retention properties.

EXAMPLE 3

A styling mousse of the following composition was prepared:

| | |
|---|---|
| Nonionic guar gum modified with hydroxypropyl groups, sold under the trade name Jaguar HP60 by the company Meyhall | 0.5 g |
| Gantrez ES 425 (ISP) 100% neutralized with AMP | 2 g AM |
| Luviskol VA 64 (BASF) | 1 g |
| Ethyl alcohol | 10 g |
| 2-Amino-2-methyl-1-propanol | qs pH 7 |
| Fragrance, preserving agent | qs |
| Demineralized water | qs 100 g |

Aerosol Packaging:

90 g of the above composition are packaged in an aerosol container in the presence of 10 g of a ternary mixture of n-butane, isobutane and propane (23/55/22), sold under the name "Aerogaz 3.2 N" by the company Elf Aquitane.

This mousse has a very pleasant creamy texture.

This mousse was applied to wet hair; it spreads easily over the entire head of hair and facilitates disentangling of the hair.

After blow-drying the hair, the hairstyle obtained is bouffant and the hair is shiny, has no residue and has a natural feel.

The hairstyle has good shape retention over time.

EXAMPLE 4

A styling mousse of the following composition was prepared:

| | |
|---|---|
| Nonionic guar gum modified with hydroxypropyl groups, sold under the trade name Jaguar HP60 by the company MEYHALL | 0.5 g |
| Luvimer (BASF) 100% neutralized with AMP | 1 g AM |
| Luviskol VA 64 (BASF) | 0.8 g |
| Ethyl alcohol | 10 g |
| Triacetin | 0.33 g |
| 2-Amino-2-methyl-1-propanol | qs pH 7 |
| Fragrance, preserving agent | qs |
| Demineralized water | qs 100 g |

Aerosol Packaging:

90 g of the above composition are packaged in an aerosol container in the presence of 10 g of a ternary mixture of n-butane, isobutane and propane (23/55/22), sold under the name "Aerogaz 3.2 N" by the company Elf Aquitane.

This mousse has a very pleasant creamy texture.

This mousse was applied to wet hair; it spreads easily over the entire head of hair and facilitates disentangling of the hair.

After blow-drying the hair, the hairstyle obtained is bouffant and the hair is shiny, has no residue and has a natural feel.

The hairstyle has good shape retention over time.

EXAMPLE 5

A gel of the following composition was prepared:

| | |
|---|---|
| Nonionic guar gum modified with hydroxypropyl groups, sold under the trade name Jaguar HP60 by the company Meyhall | 0.95 g |
| Anionic polymer 100% neutralized with AMP | 1 g AM |
| Water | qs 100 g |

Anionic Polymer:
  Gel (7) : Gantrez ES 425 (ISP)
  Gel (8) : Acrylic acid/ethyl acrylate copolymer (Luvimer MAE from BASF)
  Gel (9) : Sodium acrylate/vinylcarbinol copolymer (Hydagen FN from Henkel)

0.5 g of gel per g of hair was applied to locks of washed and towel-dried hair. The hair was then blow-dried.

A panel of 8 judges was then asked to evaluate the holding of the hairstyle and the feel of hair.

The results (average of the ratings) are collated in the following table:

| | Holding of the style | Feel |
|---|---|---|
| Gel (7) Invention | 4 | 4 |
| Gel (8) Invention | 3.5 | 2.25 |
| Gel (9) Comparative | 2.5 | 2 |

The gels (7) and (8) according to the invention have better properties of style-holding and of feel.

EXAMPLE 6

A styling gel of the following composition was prepared:

| | |
|---|---|
| Nonionic guar gum modified with hydroxypropyl groups, sold under the trade name Jaguar HP60 by the company Meyhall | 0.95 g |
| Methacrylic acid/lauryl methacrylate/vinylpyrrolidone (Acrylidone LM from ISP) | 2 g AM |
| Ethyl alcohol | 10 g |
| 2-Amino-2-methyl-1-propanol | qs pH 7 |
| Fragrance, preserving agent | qs |
| Demineralized water | qs 100 g |

This gel was applied to wet hair; it spreads easily over the entire head of hair and facilitates disentangling of the hair.

After blow-drying, the hairstyle obtained is bouffant and the hair is shiny and has no residue.

The hairstyle has good shape retention over time.

What is claimed is:

1. A non-washing cosmetic composition comprising, in a cosmetically acceptable medium, at least one nonionic guar gum and at least one non-crosslinked anionic copolymer:
    comprising (i) at least one unit of maleic acid, and (ii) at least one unit of at least one monomer selected from vinyl esters, vinyl ethers, vinyl halides, phenylvinyl derivatives, acrylic acid, and acrylic acid esters.

2. A composition according to claim 1, wherein said at least one nonionic guar gum is modified with $C_1$–$C_6$ hydroxyalkyl groups.

3. A composition according to claim 2, wherein said $C_1$–$C_6$ hydroxyalkyl groups are selected from hydroxymethyl, hydroxyethyl, hydroxypropyl and hydroxybutyl groups.

4. A composition according to claim 2, wherein said at least one nonionic guar gum has a degree of hydroxyalkylation ranging from 0.4 to 1.2.

5. A composition according to claim 1, wherein said acrylic acid esters are $C_1$–$C_{20}$ alkyl acrylates.

6. A composition according to claim 1, wherein said at least one nonionic guar gum is present in a concentration ranging from 0.01% to 5% by weight relative to the total weight of the composition.

7. A composition according to claim 1, wherein said at least one non-crosslinked anionic polymer is present in a concentration ranging from 0.01% to 8% by weight relative to the total weight of the composition.

8. A composition according to claim 1, wherein said at least one nonionic guar gum/at least one non-crosslinked anionic polymer weight ratio is less than 1:1.

9. A composition according to claim 1, wherein said cosmetically acceptable medium is selected from water and a mixture of water and at least one cosmetically acceptable solvent.

10. A composition according to claim 1, wherein said composition further comprises at least one additional component selected from surfactants, thickeners, preserving agents, sequestering agents, softeners, fragrances, dyes, viscosity modifiers, foam modifiers, foaming agents, foam stabilizers, pearlescent agents, moisturizing agents, antidandruff agents, antiseborrhoeic agents, sunscreens, proteins, vitamins, plasticizers, hydroxy acids, electrolytes, propellants, fragrances and conditioners.

11. A composition according to claim 1, wherein said composition is a form selected from a gel, a milk, a cream, a cream-gel, a spray, a relatively thickened lotion and a mousse.

12. A process for treating keratin substance with a non-washing cosmetic, comprising the steps of:
    applying the non-washing composition of claim 1 to said keratin substance, and optionally removing said non-washing composition from said keratin substance,
        wherein said optional removing step can occur either after leaving said non-washing composition an said keratin substance for a period of time or immediately after said applying step.

13. A process according to claim 12, wherein said keratin substances is hair or eyelashes.

14. A composition according to claim 6, wherein said at least one nonionic guar gum is present in a concentration ranging from 0.1% to 2.5% by weight relative to the total weight of the composition.

15. A composition according to claim 7, wherein said at least one non-crosslinked anionic polymer is present in a concentration ranging from 0.1% to 3% by weight relative to the total weight of the composition.

16. A composition according to claim 9, wherein said at least one cosmetically acceptable solvent is selected from monoalcohols, polyalcohols, glycol ethers and fatty acid esters.

17. A non-washing cosmetic composition comprising, in a cosmetically acceptable medium, at least one nonionic guar gum and at least one non-crosslinked anionic copolymer wherein said at least one non-crosslinked anionic copolymer comprises:
    a copolymer obtained from the polymerization of: (i) maleic acid, and (ii) at least one monomer selected from vinyl esters, vinyl ethers, vinyl halides, phenylvinyl derivatives, acrylic acid, and acrylic acid esters.

* * * * *